United States Patent
Nöhl et al.

[11] Patent Number: 6,119,684
[45] Date of Patent: *Sep. 19, 2000

[54] AEROSOL INHALER

[75] Inventors: Klaus Nöhl; Harald Sprenger, both of Ingelheim am Rhein, Germany

[73] Assignee: Boehringer Ingelheim KG, Ingelheim, Germany

[ * ] Notice: This patent issued on a continued prosecution application filed under 37 CFR 1.53(d), and is subject to the twenty year patent term provisions of 35 U.S.C. 154(a)(2).

[21] Appl. No.: 08/765,466

[22] PCT Filed: Jun. 21, 1995

[86] PCT No.: PCT/EP95/02410

§ 371 Date: Jun. 19, 1997

§ 102(e) Date: Jun. 19, 1997

[87] PCT Pub. No.: WO96/00595

PCT Pub. Date: Jan. 11, 1996

[30] Foreign Application Priority Data

Jun. 29, 1994 [DE] Germany .............. 44 22 710

[51] Int. Cl.[7] .................................. A61M 11/00
[52] U.S. Cl. ................. 128/200.14; 128/200.23; 128/204.23; 128/205.23
[58] Field of Search .............. 128/200.24, 200.14, 128/200.23, 203.12, 204.21, 204.23, 205.23

[56] References Cited

U.S. PATENT DOCUMENTS

| | | | |
|---|---|---|---|
| 5,284,133 | 2/1994 | Burns et al. | 128/200.23 |
| 5,331,953 | 7/1994 | Andersson et al. | 128/200.14 |
| 5,363,842 | 11/1994 | Mishelevich et al. | 128/200.14 |

FOREIGN PATENT DOCUMENTS

| | | |
|---|---|---|
| WO9207599 | 10/1991 | WIPO . |
| WO9215353 | 3/1992 | WIPO . |
| WO9217231 | 3/1992 | WIPO . |

*Primary Examiner*—Aaron J. Lewis
*Attorney, Agent, or Firm*—Robert P. Raymond; Alan R. Stempel; Mary-Ellen M. Devlin

[57] ABSTRACT

In an aerosol inhaler it is proposed that a thermal sensor 5 be arranged in the region of the atomization nozzle 4, which sensor, following the actuation of an actuating element and the triggering of an inhalation process, undergoes cooling as a result of the expansion of the propellant which then occurs. The actuation and cooling are electronically detected in an electronic module 3. Technical and therapeutic data can be derived from the signal, which data are communicated to the user via the display unit and/or alarm devices and influence the therapy in the desired manner.

1 Claim, 5 Drawing Sheets

AEROSOL INHALER

The invention relates to an aerosol inhaler for a medicinal substance to be inhaled and to an electronic module for use in association with such an inhaler.

An aerosol inhaler is to be understood as a device with the aid of which a patient can actively breathe in a given dose of a medicinal substance to be inhaled. A typical application for such a device is an acute asthma attack. Upon the actuation of a corresponding actuating element, the aerosol, consisting of a propellant and of the medicinal substance present in said propellant and distributed therein, passes from the supply container provided therefor, through a nozzle, into the air channel of a mouthpiece from where it is actively inhaled by the patient. The aerosol emission and atomization can be triggered electronically or mechanically.

Previously it was not possible to detect whether, upon the actuation of the actuating element, atomization had actually taken place or not. For example, this can be prevented by obstruction of the nozzle. Naturally atomization also does not take place when the aerosol supply container is empty. This can lead to complications as the patient has supposedly inhaled the medicine necessary to combat an acute attack, whereas in fact this is not true or only partially true. An only partial supply of the given dose frequently gives rise to a desire on the part of the patient to augment the effect of the medicinal substance by further inhalation. This can lead to a dangerous situation as a result of overdosing. Furthermore, the doctor caring for the patient loses an overview of the number of doses administered within a predetermined time interval, which is an impediment to responsible medical treatment.

Therefore, with this background, the object of the present invention is to further develop an aerosol inhaler of the type defined in such manner that it is at least possible to reliably recognise and evaluate the atomization of the aerosol upon the actuation of the actuating element. In accordance with further aspects of the invention, a series of evaluations relating to some treatment parameters, such as the number of administered doses, the doses remaining in the supply container and the indication thereof, as well as for example the checking of the aerosol to determine whether it corresponds to the doctor's prescription, are to be possible. Furthermore, an electronic module is to be provided for use in association with such an inhaler, which electronic module fulfils the electronic part of the object of the invention but in principle can also be used in the case of all known aerosol inhalers, and thus as an accessory to an aerosol inhaler.

In accordance with the invention, it is thus provided that the inhaler be equipped with an electronic module which comprises an evaluating electronic unit for function monitoring which is supplied with signals from at least one thermal sensor arranged in the flow region of the nozzle and from a device for recognising the actuation of the actuating element, and comprises a display device for the output of the evaluation result produced by the evaluating electronic unit.

The crux of the invention thus consists in that a thermal sensor is arranged directly on the nozzle in which the atomization of the aerosol takes place. This permits a positive detection of the atomization of the aerosol on the basis of the recognition of the actuation and of the cooling of the propellant which occurs upon atomization, in that the cooling of the propellant leads to the cooling of the thermal sensor and a clearly defined electric signal can be generated. Malfunctions, such as obstructed nozzles or an empty aerosol supply container, can thus be reliably detected.

In a special and simple exemplary embodiment, the evaluating electronic unit generates a warning signal when atomization does not take place, and a signal representing the number of inhalation doses still contained in the supply container. These signals are communicated to the patient by means of a suitable display or, in the case of the warning, with an acoustic signal. As a result of the monitoring of the atomization the user can be warned when no atomization has occurred and thus he has not inhaled any medicinal substance, as can happen when a supply container is empty or also in particular when a nozzle is obstructed.

In accordance with a further advantageous development, it is provided that the thermal sensor detects the air flowing past it at the start of the inhalation, generates a corresponding signal therefrom, and sends this signal to the evaluating electronic unit which itself generates a signal which is optically and/or acoustically displayed as a coordination aid for the patient in the inhalation process.

The background to this further development is as follows:

The correct inhalation of the aerosol ideally proceeds in such manner that, having exhaled, the patient applies the device to his mouth and after the start of the inhalation triggers the atomization by depressing the actuating element. Many users have problems however in coordinating their breathing and the triggering of the atomization. An incorrect timing sequence of inhalation and triggering diminishes the effect of the medicament however, and impairs the clinical result. It is here that the described further development comes into effect in that immediately following the start of the inhalation the patient is informed by means of the optical or acoustic display that atomization is imminent. In this way the clinical result of the treatment is distinctly improved.

In accordance with a further embodiment it is provided that a further thermal sensor is arranged outside of the flow path of the aerosol, which further thermal sensor generates a reference signal which is likewise fed to the evaluating electronic unit and is linked with the signal from the first thermal sensor in such manner that the result permits the emitted quantity of aerosol to be deduced. The linking can take place, for example, in a differential amplifier in which it is possible to form the time characteristic of the difference between the temperature of the first thermal sensor arranged directly on the nozzle and the environmental temperature. The downstream, evaluating electronic unit then receives this difference signal and the integration of said signal within suitable limits supplies a value which, with the aid of a relation stored in a memory of the evaluating electronic unit, leads to the atomized quantity of aerosol. As a result of the quantitative detection, after each inhalation the patient can be given precise information as to whether a further inhalation is necessary. In the event of the undershooting of a specified quantity, preset in the program of the evaluating electronic unit, a warning signal can be generated which informs the patient that too little active ingredient has been inhaled. This monitoring possibility leads to greater reliability in the use of inhalers and to a more efficient therapy.

Alternatively, the emitted quantity of aerosol can be determined in that prior to the atomization the environmental temperature of the thermal sensor, which is anyhow arranged in the region of the nozzle, can be detected, digitalized and stored in the evaluating electronic unit. When the aerosol is now atomized during inhalation, the time characteristic of the temperature changes of the sensor is detected as so-called temperature profile. This temperature profile is digitalized and the previously stored environmental temperature is subtracted therefrom. The integration of the difference within suitable limits supplies a value which, with the aid of a relation stored in the memory of the evaluating electronic unit, leads to the atomized quantity of aerosol. The relation between the output voltage of the sensor signal amplifier and the temperature of the sensor can be stored in the memory of the evaluating electronic unit. Any non-linearities of the sensor and the signal amplifier, and thus also the influence of shifts in operating point, caused by changes in the environmental temperature, can be computationally eliminated in the evaluating electronic unit.

If, in accordance with a further embodiment, the evaluating electronic unit comprises a microcontroller, the latter is preferably assigned a memory for the storage of data as well as a serial interface for communication with an external computer.

This embodiment provides the doctor in charge with the possibility, entirely novel in the relevant field, of monitoring whether the patient has actually inhaled the number of inhalation doses prescribed by him, and the time interval within which this has taken place. An abundance of data to be input into the memory, and functions associated therewith, are possible. Thus for example the doctor can also predetermine a time interval after which a further inhalation is to take place, and by means of a real-time clock present in the module an optical and/or acoustic signal is generated to remind the patient of the further inhalation.

The functions can be monitored and the implementation or non-implementation thereof can likewise be stored in the memory. On the occasion of a further visit to the doctor in charge, this data can then be read out via the serial interface and interpreted by the doctor. For the input into and output from the memory, the electronic module is to be connected via the serial interface—as already mentioned—to an external computer.

The presence of the evaluating electronic unit in the inhaler according to the invention facilitates further functions; in accordance with another embodiment the aerosol supply container can consist of a replaceable part so that it is detachably insertable into the inhaler. The exterior of the detachable supply container can have optically coded surfaces, such as are known for example in connection with the so-called DX-coding of miniature film cartridges in photography. The evaluating electronic unit is then designed in such manner that it can decode the information contained in this code. This information can for example indicate the type of active ingredient of the medicinal substance in the aerosol and the expiry date thereof. This data can be read out and compared in the microcontroller of the evaluating electronic unit for example with the information relating to the type of active ingredient input by the doctor. In the event of differences, an alarm signal can be triggered. The aforementioned real-time clock in the electronic module can be used to check the expiry data of the medicinal substance in the aerosol and to trigger an alarm when the expiry date is exceeded.

In this embodiment the replaceable supply container can also itself comprise an electronic memory; the data stored in this memory can be read out by the evaluating electronic unit and the evaluating electronic unit can input data into this memory. This memory can be provided in addition to the aforesaid optical coding or also by itself. For the data exchange between the inhaler and an external computer located, for example, at the doctor's premises, a plug-in EEPROM module which retains its data without a power supply can be used. The external computer has an adapter via which data can be input into the EEPROM module and also read out from the latter. Via this storage module, on the one hand the information concerning the type of active ingredient and the prescribed treatment can be communicated to the device and on the other hand the device itself inputs the therapy actual data therein.

In another embodiment a sensor contact can be arranged on the mouthpiece of the inhaler. The signal from this sensor contact is fed to the evaluating electronic unit. It is thus possible to check whether, in the case of correct atomization, the patient has actually received the medicinal substance. This ensures that an atomization which, although correct, has been released into space and thus has not reached the patient, is not recorded in the memory as an administered dose.

Here it should again be emphasised that all the aforementioned monitoring possibilities are conditional upon the inhaler being provided with a thermal sensor directly on the nozzle where the aerosol is atomized, and with a device for recognising the actuation of the actuating element and with an evaluating electronic unit which evaluates the signals from this sensor and from the actuation-recognition device. The electronic module referred to in the introduction, as a part which is to be handled independently of the actual inhaler and which can itself constitute a commercial article, is provided in accordance with the invention with a separate housing which can be detachably secured to the inhaler and comprises, projecting away from itself, the at least one thermal sensor which is to be arranged in the direct vicinity of the nozzle opening in the inhaler.

The electronic module can be produced and tested independently of the inhaler. Only in the last production step is the electronic module clipped onto the device and the complete device subjected to final testing. However, it can also be marketed separately, independently of a concrete type of inhaler and serve as accessory.

In accordance with an advantageous further development the aforementioned second thermal reference sensor is also arranged on the electronic module, whereby the unit as a whole becomes very compact as this second sensor is not to be applied, for example, to the inhaler, which indeed would additionally require the establishment of an electric connection.

The thermal sensor or sensors is/are preferably NTC resistors, thermistors or surface thermoelements, i.e. elements whose electrical properties change in an evaluatable manner in the event of a change in temperature.

The evaluating electronic unit can be formed by a microcontroller or a customised circuit in which all the necessary electronic functions are integrated. This design allows a reduction in the space required for the evaluating electronic unit and the power requirement and—due to the associated reduction in the battery volume—in the overall volume of the electronic module. The circuit board of the electronic module advantageously can be constructed in accordance with SMD technology. For reasons of space and costs the microcontroller can be assembled without the use of an IC housing in accordance with chip-on-board (COB)—or tape-automated-bonding (TAB) technology. The display unit and necessary batteries are fixed on the circuit board via a clip-on plastics frame and electrically connected to the circuit board via conductive rubber and contact springs.

The switching on and off of the device can take place without an additional operating step by the removal and application of the inhaler cap. If the cap remains open for a relatively long time interval, after a specified time the electronic unit is automatically switched to a so-called "sleep mode" and is automatically "awoken" by the triggering of an inhalation. When the cap is in place, mechanical locking can be provided which prevents the triggering of the atomization.

The display unit can preferably consist of a LCD with a 3-digit, 7-segment display and a symbol for the daily dose warning, battery warning and display of a device fault.

When a newly filled aerosol supply container is inserted in the inhaler, it is necessary to actuate a reset pushbutton on the electronic module whereby the remaining dose is set at a value corresponding to a full container. This function can also be implemented, in accordance with another embodiment, by means of the actuation-recognition device which sends a signal to the evaluating electronic unit both when the actuating element is activated and when the container is changed. The reset pushbutton is then not required.

The inhalation process of the inhaler according to the invention can also be electronically triggered. The electronic unit required for this purpose can likewise be accommodated in the electronic module. Incorrect triggerings are substantially prevented by a sensor contact on the mouthpiece.

The electronic recognition of the inhalation phase, referred to in the foregoing, by means of the thermal sensor in the flow region of the nozzle can also be used to trigger the atomization fully automatically via the breath. For this purpose, after a corresponding signal evaluation, the evaluating electronic unit sends a signal to the actuating element of the inhaler and thus triggers the atomization. The coordination is then assumed in full by the device. The patient need only apply the device to his mouth and inhale.

The evaluation of the sensor signal can also take place in that, after amplification, the analogue signals are immediately digitalized, the function of the above described comparators is assumed by the program of the evaluating electronic unit, and the corresponding switching levels and delay times are determined by the program.

In the following the inhaler according to the invention will be explained in detail in the form of an exemplary embodiment. In the drawings:

FIGS. 1 to 3 are views of the inhaler according to the invention which represent only principal diagrams and do not correspond to actual sectional illustrations.

Figure 1:
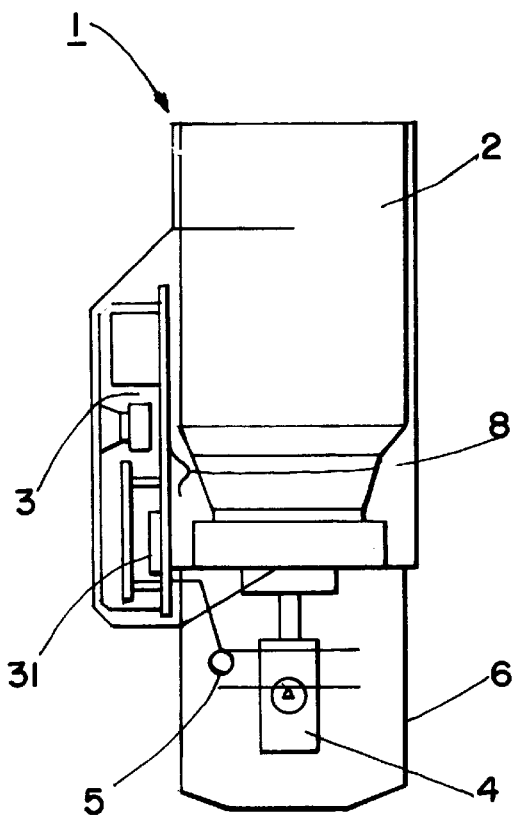
FIG. 1 is a front view of the inhaler with electronic module clipped-on laterally.
Figure 2:
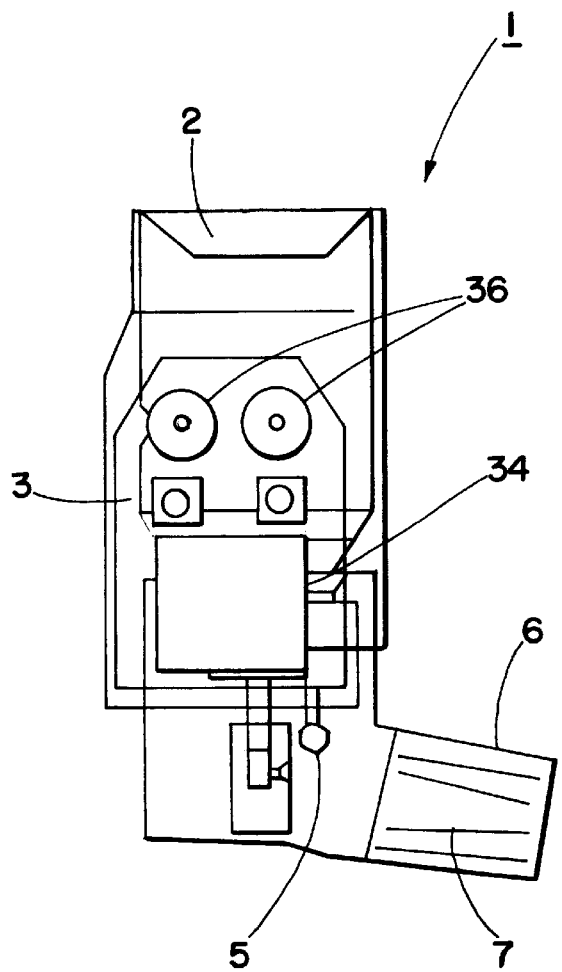
FIG. 2 is a side view of the inhaler according to FIG. 1.
Figure 3:
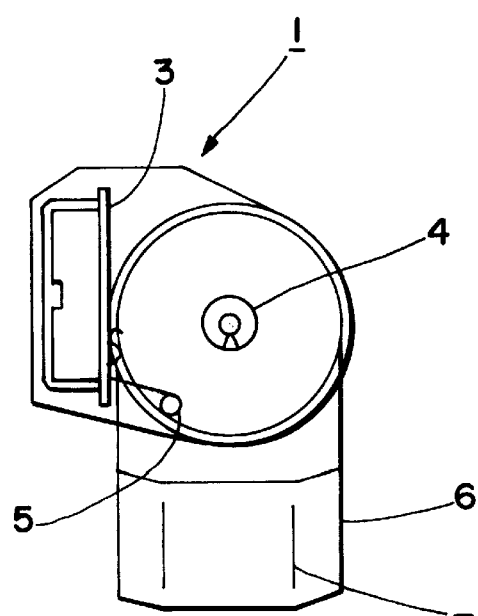
FIG. 3 is a plan view of the device according to FIGS. 1 and 2.
Figure 4:
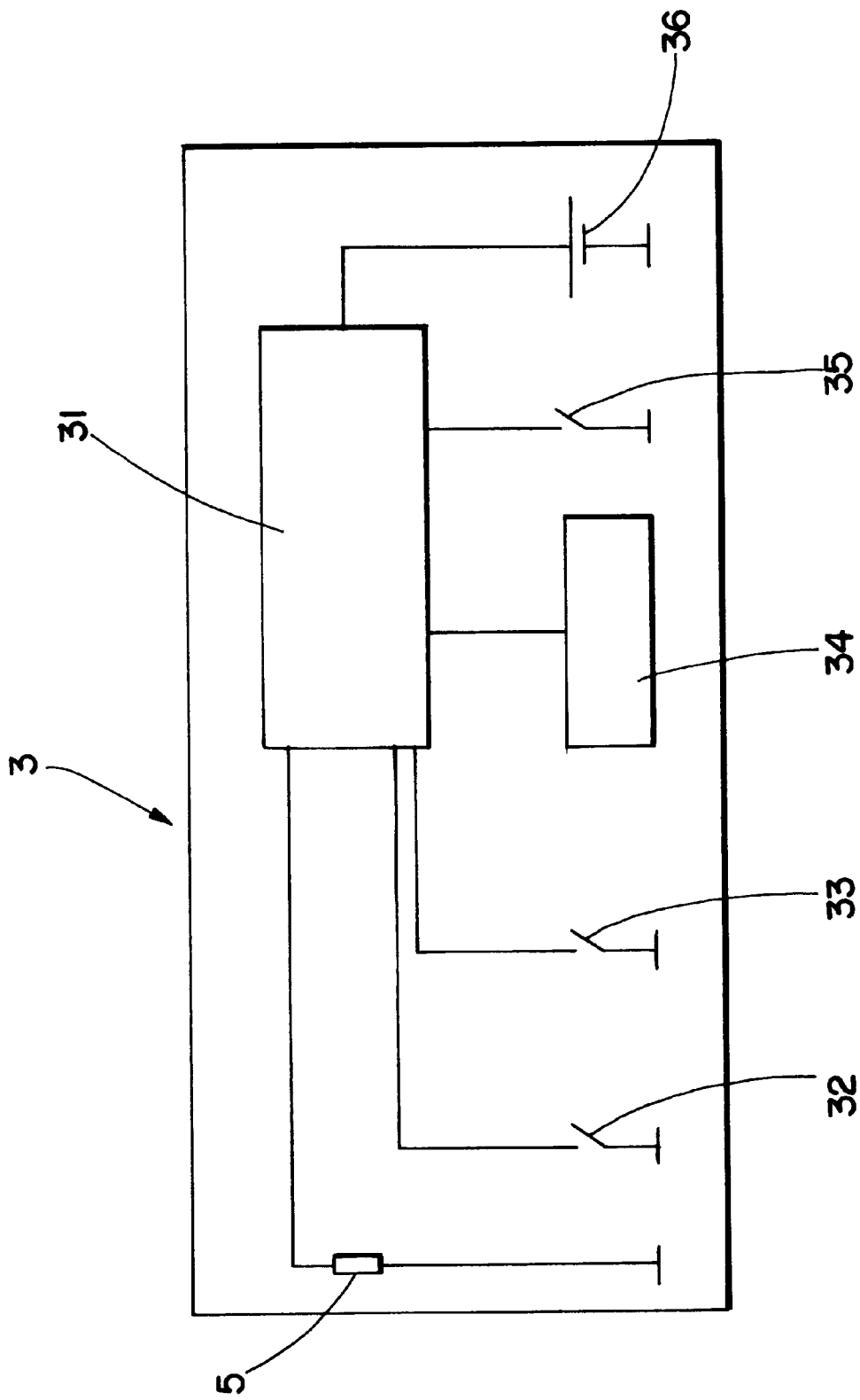
FIG. 4 is a principal circuit diagram of the evaluating electronic unit.
Figure 5A:
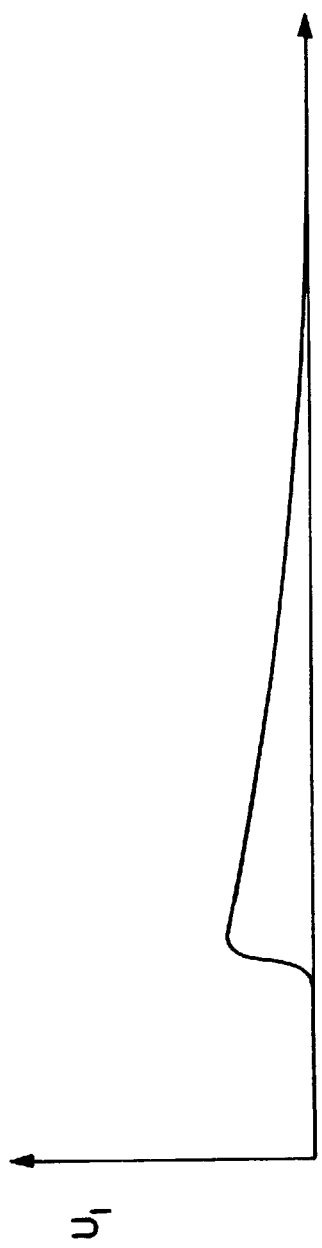
FIGS. 5a to 5c show time characteristics of output signals.
Figure 5B:
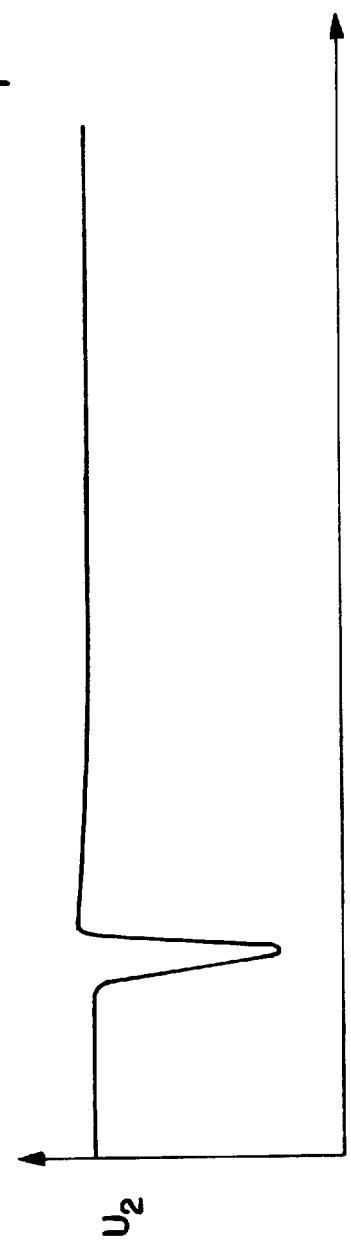
Figure 5C:
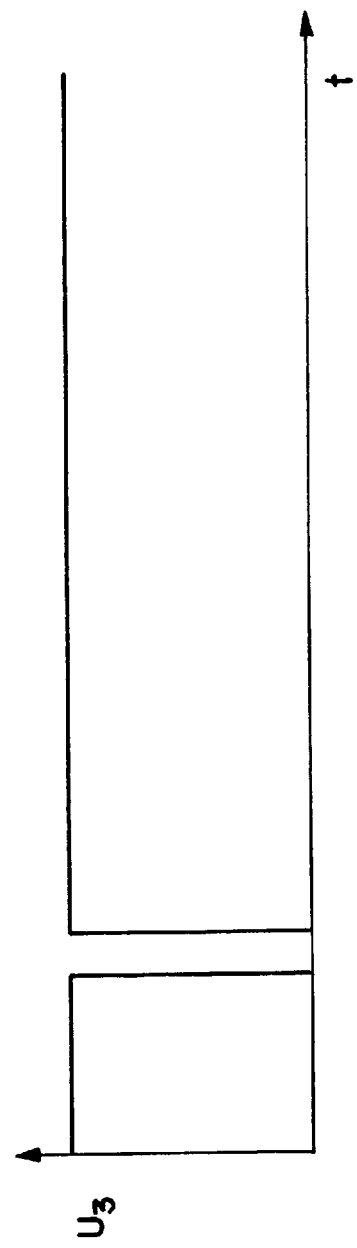
Figure 6:
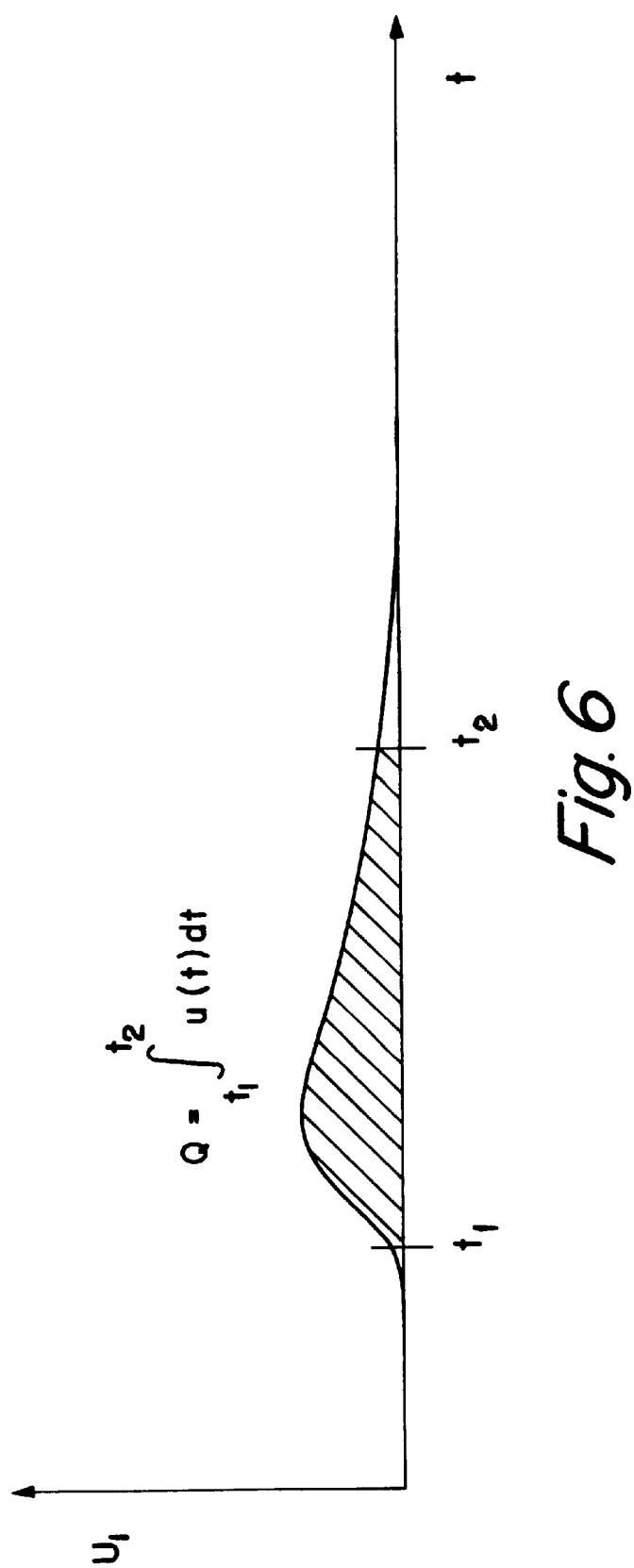
FIG. 6 shows a time characteristic of the integration of the difference signal between the thermal sensor at the nozzle opening and the reference sensor.

The inhaler 1 according to the invention comprises a supply container 2 for an aerosol. In the present case the supply container 2 is detachably connected to a housing which has a mouthpiece 6 with air channel 7 extending therein. By means of an actuating element (not shown here) a dose of the aerosol is inlet from the supply container 2 into the nozzle 4 where it is atomized. The patient breathes in this atomized aerosol through the air channel 7.

During this process the supply container 2 moves and via the actuation-recognition device 8 releases a signal which is fed to the evaluating electronic unit 31. The first thermal sensor 5 is arranged directly at the opening of the nozzle 4. When an atomization from the nozzle 4 takes place, the propellant expands and the temperature in the region of the nozzle opening falls. This fall in temperature is detected by the thermal sensor 5, which latter generates a corresponding signal which is likewise fed to the evaluating electronic unit 31.

As already mentioned, in the present case the electronic module 3 is clipped onto the inhaler 1 and can be handled independently. It is of compact construction and contains all the necessary components, of which the batteries 36 and the optical display unit 34 have been provided with reference symbols in FIGS. 1 to 3. The optical display unit preferably consists of a 3-digit, 7-segment LCD display. The principal circuit diagram of the evaluating electronic unit 30 is shown in FIG. 4.

In the present case the main component is an evaluating electronic unit 31 which is supplied with the signal from the actuation-recognition device 8 and the signal from the thermal sensor 5. The evaluating electronic unit is not activated until the contact 33 is closed, which occurs when the cap of the device has been removed.

The circuit is supplied by the battery 36. In the present case the display takes place via the aforementioned display unit 34.

Finally a reset switch 35 is also provided, which must be actuated when a newly filled supply container is inserted into the inhaler 1 so that the remaining dose is set, in the memory of the evaluating electronic unit 31, at a value corresponding to a full supply container.

The signal processing will be briefly explained with reference to FIGS. 5 and 6.

FIG. 5*a* illustrates the curve of the voltage $U_1$ across the thermal sensor 5. Upon the expansion of the propellant in the nozzle 4 and the accompanying cooling of the sensor 5, the voltage $U_1$ initially rises steeply and after the atomization process falls to its original value in accordance with the thermal time constant.

FIG. 5*b* shows the time characteristic of an output voltage $U_2$ of a frequency-selective amplifier, to the input of which the voltage $U_1$ from FIG. 5*a* is applied. It can be seen that $U_2$ has a pronounced pulse in the case of atomization (event).

The voltage $U_2$ is fed for example to a comparator which in the rest state has a constant positive output voltage and in the case of correct atomization emits a negative pulse and at the time of an event temporarily assumes the voltage zero. The voltage $U_3$ is the digital input signal for the evaluating electronic unit. Amplifier and comparator can form part of the evaluating electronic unit.

Finally FIG. 6 shows the possibilities of electronic evaluation when a further thermal sensor (not shown) is provided as reference sensor which is exposed to the environmental temperature. Thus with the aid of a differential amplifier it is possible to form the time characteristic of the difference between the environmental temperature and the temperature of the nozzle 4 in the inhaler 1 and to supply this time characteristic to an analogue-digital converter of a processor contained in the microcontroller. The integration of this signal $U_1$ from FIG. 6 within suitable limits $t_1$ and $t_2$ supplies a variable $$Q' = \int_{t_1}^{t_2} u_1(t)\,dt$$

which, with the aid of a clearly defined relation stored in a ROM storage module of the processor, leads to the actually atomized quantity of aerosol Q.

Finally FIG. 7 shows the signal processing in the event that, in accordance with a further development, the recognition of the inhalation phase is electronically evaluated.

The frequency-selective amplifier provided for the atomization recognition is preferably used for the signal processing.

Figure 7A:
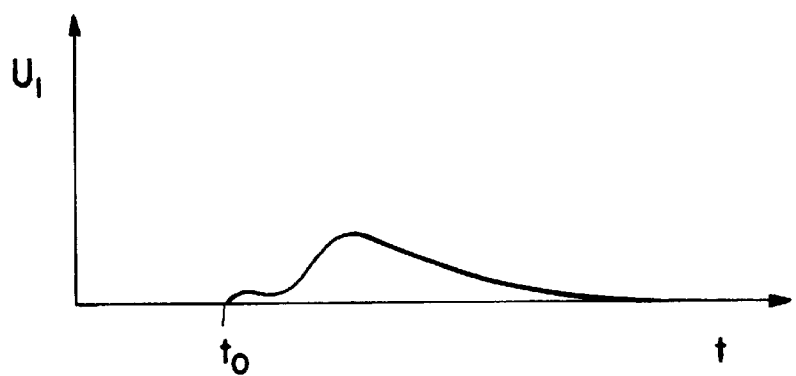
FIG. 7 illustrates further time characteristics of output signals in the case of which the inhalation phase is electronically evaluated.
Figure 7B:
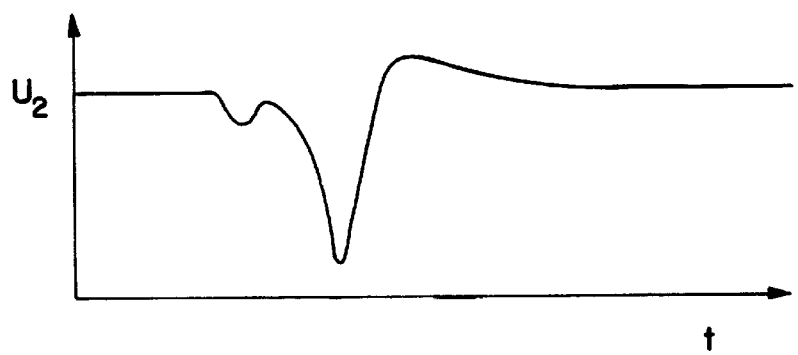
Figure 7C:
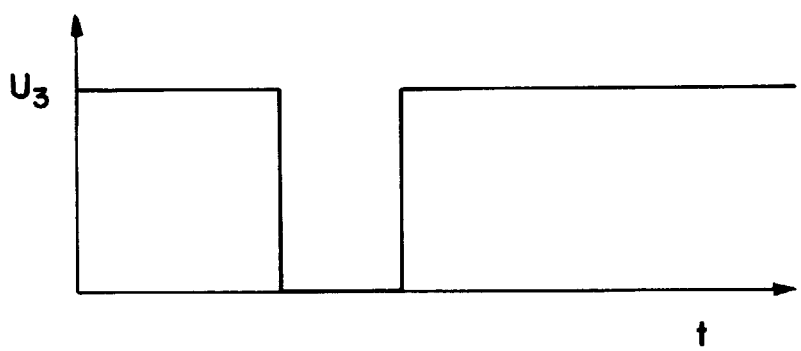
Figure 7D:
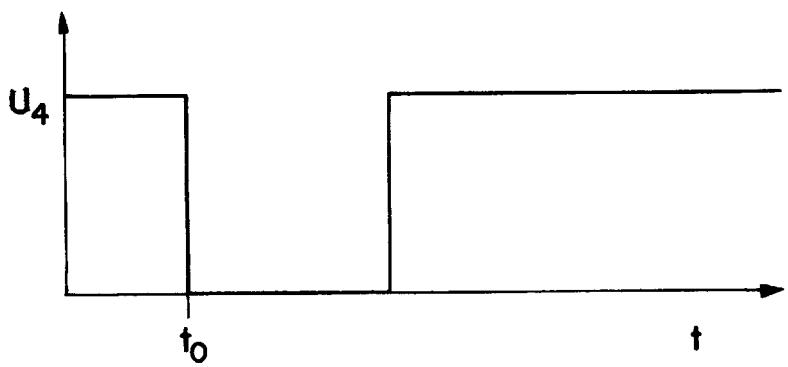

FIG. 7a shows the time characteristic of the voltage $U_1$ across the thermal sensor, FIG. 7b shows the characteristic of the voltage $U_2$ at the output of the selective amplifier, FIG. 7c shows the characteristic of the voltage $U_3$ at the output of the comparator for the atomization recognition and FIG. 7d shows the time characteristic of the voltage $U_4$ at the output of a further comparator for the duration of a breathing-in and inhalation phase with correct atomization.

The voltage $U_1$ across the thermal sensor firstly has a small pulse, the front flank of which represents the start of the inhalation, i.e. when the first inhalation air passes the thermal sensor 5. The output voltage $U_2$ of the frequency-selective amplifier here already has an extremely marked pulse however. The voltage is fed to a comparator whose output voltage $U_4$ is the digital input signal for the evaluating electronic unit 31. The front flank of the voltage $U_4$ coincides with the start of the inhalation ($t_0$). After a delay time, freely defined in the program of the evaluating electronic unit 31, for this flank, the evaluating electronic unit 31 emits an acoustic signal via an electromechanical transducer (for example a piezoelectric oscillator).

The continued course of the voltage $U_1$, namely in a more strongly positive ascent, and of the voltage $U_2$ with the strongly negative pulse result from the cooling of the thermal sensor 5 due to the correct atomization of the aerosol which follows the triggering. The output voltage $U_3$ of the corresponding comparator then has a negative pulse which is fed to the evaluating electronic unit.

For the patient, handling is simplified in that he starts to inhale having applied the inhaler to his mouth, and not until he hears a signal does he trigger the atomization by actuating the actuating element. This ensures that the patient does not trigger the atomization for example immediately after having applied the inhaler to his mouth and then inhale, or does note trigger the atomization when the inhalation phase is over, but triggers the atomization correctly with the inhalation. This serves to favourably influence the effects of the medicament.

The invention is not limited to the concrete exemplary embodiment explained here but includes all the possibilities, described in the foregoing, relating to the use and evaluation of the detected data.

What is claimed is:

1. An improvement in an inhaler for the administration by inhalation of an aerosol consisting of a medicament an a propellant, said inhaler being of a known design comprising:

a) a supply container having propellant and medicament therein;

b) a nozzle for atomizing propellant and medicament conveyed thereto, to form an aerosol therefrom, having an opening from which the aerosol so formed is expelled;

c) means for conveying propellant from the supply container to the nozzle;

d) an actuating element for causing the conveyance of propellant and medicament from the supply container to the nozzle, upon actuation by a user of the inhaler; and, e) a mouthpiece having a channel, through which the aerosol formed by the nozzle is expelled from the inhaler, so that it may be inhaled;

wherein the improvement comprises the addition of an an electronic means for sensing and reporting whether aerosol has been expelled from the inhaler upon actuation by the user, said electronic means comprising:

f) a first thermal sensor, located in the vicinity of the nozzle opening, which produces an electrical signal that varies in response to the temperature in the vicinity of the nozzle opening, including any decrease in temperature caused by the expuslion of aerosol from the nozzle opening;

g) a second thermal sensor, located away from the vicinity of the nozzle opening, for developing a reference signal which represents the ambient temperature and which is not influence by the expulsion of aerosol from the nozzle opening;

h) an actuation-recognition device for producing an electrical signal upon actuation of the actuating means;

i) an evaluating electronic unit, connected to the first thermal sensor, the second thermal sensor and the actuation recognition device, which evaluating electronic unit compares the signals of the two thermal sensors in order to determine whether there has been a decrease in temperature in the vicinity of the nozzle opening, and which uses the signal from the the actuation recognition device to evaluate whether a decrease in temperature in the vicinity of the nozzle opening has coincided with actuation of the actuating means, and which thereby determines whether aerosol has been expelled from the inhaler upon actuation by the user; and, j) an electronic display, by means of which the determination of the evaluating electronic unit is reported.

* * * * *